United States Patent
Brazdil et al.

(10) Patent No.: US 12,162,817 B2
(45) Date of Patent: *Dec. 10, 2024

(54) PROCESSES AND CATALYST SYSTEMS FOR PRODUCING MONOETHANOLAMINE FROM GLYCOLALDEHYDE

(71) Applicant: Archer Daniels Midland Company, Decatur, IL (US)

(72) Inventors: James Brazdil, Glen Ellyn, IL (US); Chi-Cheng Ma, Champaign, IL (US)

(73) Assignee: ARCHER-DANIELS-MIDLAND COMPANY, Decatur, IL (US)

(*) Notice: Subject to any disclaimer, the term of this patent is extended or adjusted under 35 U.S.C. 154(b) by 925 days.

This patent is subject to a terminal disclaimer.

(21) Appl. No.: 17/265,054

(22) PCT Filed: Jul. 30, 2019

(86) PCT No.: PCT/US2019/044073
§ 371 (c)(1),
(2) Date: Feb. 1, 2021

(87) PCT Pub. No.: WO2020/028322
PCT Pub. Date: Feb. 6, 2020

(65) Prior Publication Data
US 2021/0309604 A1 Oct. 7, 2021

Related U.S. Application Data (60) Provisional application No. 62/713,777, filed on Aug. 2, 2018.

(51) Int. Cl.
| | | |
|---|---|---|
| *C07C 213/02* | (2006.01) | |
| *B01J 25/02* | (2006.01) | |
| *B01J 29/068* | (2006.01) | |
| *B01J 29/072* | (2006.01) | |
| *B01J 29/14* | (2006.01) | |
| *B01J 29/76* | (2006.01) | |

(52) U.S. Cl.
CPC .......... *C07C 213/02* (2013.01); *B01J 25/02* (2013.01); *B01J 29/068* (2013.01); *B01J 29/072* (2013.01); *B01J 29/146* (2013.01); *B01J 29/7615* (2013.01)

(58) Field of Classification Search
CPC . B01J 23/462; B01J 23/74; B01J 25/02; B01J 29/068; B01J 29/072; B01J 29/146; B01J 29/7615; C07C 213/02; C07C 215/08; Y02P 20/582
See application file for complete search history.

(56) References Cited

U.S. PATENT DOCUMENTS

| | | | |
|---|---|---|---|
| 4,153,581 | A | 5/1979 | Habermann |
| 6,696,610 | B2 | 2/2004 | Peschel et al. |
| 2012/0259139 | A1 | 10/2012 | Mgerlein et al. |
| 2012/0271068 | A1 | 10/2012 | Mgerlein et al. |

FOREIGN PATENT DOCUMENTS

| | | | |
|---|---|---|---|
| CN | 107011194 | * | 8/2017 |
| WO | WO/2020/028322 | | 2/2020 |

OTHER PUBLICATIONS

Liang, G. et al., ("Production of Primary Amines by Reductive Amination of Biomass-Derived Aldehydes/Ketones", Angew. Chem. Int. Ed, 2017, vol. 56, pp. 3050-3054, published Feb. 3, 2017). (Year: 2017).*
CN107011194 translated. (Year: 2017).*
International Preliminary Report on Patentability issued on Nov. 25, 2019 for International Application No. PCT/US2019/044073 for Applicant Archer Daniels Midland Company.
Liang, G. et al., "Production of Primary Amines by Reductive Amination of Biomass-Derived Aldehydes/Ketones", Angew. Chem. Int. Ed, 2017, vol. 56, pp. 3050-3054(published Feb. 3, 2017) See abstract, col. 3-5, Table 1.

* cited by examiner

*Primary Examiner* — Jafar F Parsa
*Assistant Examiner* — Blaine G Doletski
(74) *Attorney, Agent, or Firm* — Jesse S. Harper (57) ABSTRACT

Improvements in catalyst systems and associated processes for the conversion of glycolaldehyde to monoethanolamine are disclosed. The catalyst systems exhibit improved selectivity to this desired product and consequently reduced selectivity to byproducts such as diethanolamine and ethylene glycol. These beneficial effects are achieved through the use of acids, and particularly Lewis acids, as co-catalysts of the reductive amination reaction, in conjunction with a hydrogenation catalyst.

9 Claims, 3 Drawing Sheets

FIG. 3

PROCESSES AND CATALYST SYSTEMS FOR PRODUCING MONOETHANOLAMINE FROM GLYCOLALDEHYDE

CROSS-REFERENCE TO RELATED APPLICATIONS

This application is a national stage entry of International Application No. PCT/US19/44073, filed Jul. 30, 2019, which itself claims priority to U.S. Provisional Patent Application No. 62/713,777, filed Aug. 2, 2018, the contents of each are incorporated herein by reference.

TECHNICAL FIELD

The present invention from one perspective relates to methods for the synthesis of biobased amines, and more particularly, to methods for the synthesis of such amines which are presently also made from non-renewable resources. From another perspective, the present invention relates to methods for the production of monoethanolamine.

BACKGROUND ART

The long-term trend of increasing cost of many hydrocarbon feedstocks has created major incentives for seeking alternative sources to petroleum-based carbon for the production of many important and valuable chemical products. Biomass (material derived from living or recently living organisms) is viewed as a readily available, inexpensive supply of renewable, non-petroleum based carbon from which many such known, high value chemicals can be derived. The ability to convert biomass to fuels, chemicals, energy and other materials is expected to strengthen rural economies, decrease dependence on oil and gas resources, and reduce air and water pollution. The generation of energy and chemicals from renewable resources such as biomass also reduces the net liberation of carbon dioxide, a greenhouse gas, into the environment, from fossil-based sources of otherwise "sequestered" carbon.

Nonetheless, the development of sustainable technologies for the production from renewable resources of those chemicals that have heretofore been made from petroleum-based carbon remains a significant challenge. For example, in recent years, the biodiesel industry has provided abundant crude glycerol as a byproduct of refining triglycerides in plant oils and animal fats. This glycerol can be purified to serve as a feedstock for producing propylene glycol (1,2-propanediol), a same carbon-numbered, known high value chemical from non-renewable resources. However, significant expense resides in the steps needed to adequately purify glycerol for this purpose, and the biodiesel industry is heavily dependent on tax credits and other forms of governmental subsidies for its profitability.

As noted in a recent journal review, Froidevaux et al, "Biobased Amines: From Synthesis to Polymers; Present and Future", CHEM. REV. 116 (22): 14181-14224 (2016), amines represent a class of known, useful chemical products from petroleum-based carbon—for example, as key monomers for the synthesis of polyamides, polyureas and polyepoxides, which are all of growing interest in automotive, aerospace, building and health applications—which present still an additional challenge in that very few natural amines are available from which biobased replacements might be obtained.

The ethanolamines—monoethanolamine or 2-aminoethanol (MEA), diethanolamine (DEA) and triethanolamine (TEA)—are specific examples of known, commercially significant amines from petroleum-based carbon, specifically, through reacting ethylene oxide with aqueous ammonia to provide MEA, DEA, and TEA in admixture with one another. While the product distribution can be altered to an extent by various means, in particular, by changing the stoichiometry of the reactants, nevertheless one seeking to make MEA for natural gas scrubbing, for use in pharmaceuticals, detergents, emulsifiers, polishes, in corrosion inhibition or as an intermediate generally will also have to find profitable uses or consumers for DEA and TEA as well. Ethylene oxide as a starting material is also undesirable, posing significant toxicological, reactive safety and environmental concerns.

The Froidevaux et al. review does mention that biobased monoethanolamine has been synthesized from the amino acid serine, but the amount of serine produced annually is several orders of magnitude less than would be needed for the synthesis and supply of a biobased monoethanolamine to meet annual demand for MEA, and the necessity of producing serine implicates additional costs that would ideally be avoided.

The present state of the art would thus benefit significantly from additional, improved methods for producing biobased monoethanolamine, particularly from methods proceeding more directly from carbohydrates or via intermediates with more commensurate utility and scale of manufacture. Glycolaldehyde ($C_2H_4O_2$) is an example of just such an intermediate, having significant utility as a reactive intermediate in that it is the smallest molecule having both reactive aldehyde and hydroxyl groups, and being susceptible of production by several conversion pathways from biomass-derived carbohydrates, such as fructose or sucrose. Yet while there are a handful of precedents from years prior to very recently which describe methods for producing MEA and DEA from glycolaldehyde by reductive amination in the presence of a catalyst, see, for example, U.S. Pat. Nos. 6,534,441, 8,772,548 and 8,742,174, there remains a need for considerable improvements in selectivity and yield for the commercial scale production of a biobased MEA from glycolaldehyde to be considered reasonably economically foreseeable.

SUMMARY OF THE INVENTION

Aspects of the invention are associated with the discovery of improvements in catalyst systems for the conversion of glycolaldehyde to monoethanolamine, which catalyst systems exhibit improved selectivity to this desired product and consequently reduced selectivity to diethanolamine and byproducts such as ethylene glycol. More particular aspects relate to the beneficial effects of acids, and particularly Lewis acids, in performing reductive amination of glycolaldehyde, to selectively produce monoethanolamine. As co-catalysts of this reaction, in conjunction with a hydrogenation catalyst, Lewis acids may be included in the reaction mixture, to which glycolaldehyde and an aminating agent are added, and from which monoethanolamine is produced. Suitable Lewis acids may be homogeneous in the reaction mixture, generally such that both the co-catalyst and reaction mixture are in the liquid phase (e.g., in the case of the co-catalyst being solubilized). Alternatively, such Lewis acids may be heterogeneous, generally such that the co-catalyst is present as a solid in the reaction mixture.

In the case of both the hydrogenation catalyst and co-catalyst being solid, further advantages are gained in terms of the case of separation of the product mixture, following reaction, from the catalyst and co-catalyst. In the case of batchwise operation, this allows for simple filtration of the catalysts from the product mixture. A solid catalyst system also allows for the formulation of the catalyst and co-catalyst into particles of sufficient size to be contained in a reactor (e.g., fixed-bed reactor) with sufficiently low pressure drop as needed for the process to be performed continuously, and therefore in a manner that is more amenable to commercial operation. Continuous operation may involve continuous feeding of the reactant glycolaldehyde, for example with an aminating agent such as ammonia or aqueous ammonia (ammonium hydroxide), and also with hydrogen. These streams may be contacted with the hydrogenation catalyst and co-catalyst, contained in the reactor and operating under reductive amination conditions. Such operation may also involve the continuous withdrawal of a product mixture comprising monoethanolamine, followed by the separation of a monoethanolamine-containing product from this mixture. More particularly, the monoethanolamine-containing product may be separated from unconverted reactants and/or byproducts. At least a portion of any unconverted reactants (e.g., hydrogen) may be recycled to the reactor (e.g., using a recycle compressor to return hydrogen, in a recycle gas stream, back to the reactor). In the case of solid catalysts, this also allows for the formulation of the hydrogenation catalyst and acid co-catalyst together in solid particles, e.g., solid particles of a bi-functional catalyst having both hydrogenation activity and Lewis acid sites.

These and other aspects, embodiments, and associated advantages will become apparent from the following Detailed Description.

The figures are to be understood to present embodiments of the invention to aid in understanding of the principles and reaction chemistry involved, but not to limit the scope of the invention as defined in the appended claims. As would be apparent to one of skill in the art, with the knowledge gained from the present disclosure, reductive amination processes according to various other embodiments of the invention will utilize particular catalysts, co-catalysts, and reaction conditions determined, at least in part, according to specific objectives.

DETAILED DESCRIPTION OF EMBODIMENTS

Embodiments of the invention are directed to methods or processes for producing or synthesizing monoethanolamine from glycolaldehyde. The desired reductive amination reaction pathway can be depicted as:

The term "glycolaldehyde" is meant to encompass the compound shown above, as well as various forms that this reactive compound may undertake, such as in an aqueous environment of a reaction mixture as described herein. Such forms include glycolaldehyde dimer and oligomer forms, as well as hydrated forms. Glycolaldehyde dimer is a particularly prevalent form, and this form is also known as the ringed structure, 2,5-dihydroxy-1,4-dioxane. For purposes of determining molar selectivity to, and theoretical yield of, monoethanolamine, each mole of glycolaldehyde dimer is considered equivalent to two moles of glycolaldehyde. Similar considerations apply to other glycolaldehyde oligomers.

"Molar selectivity to monoethanolamine" is the percentage, on a molar basis, of converted glycolaldehyde, which results in the formation of monoethanolamine. The yield of monoethanolamine is the amount obtained, expressed as a percentage of the theoretical amount that would be obtained by reacting glycolaldehyde with 100% conversion and 100% molar selectivity to monoethanolamine. The yield can be determined as the product of conversion and selectivity. Therefore, if 10 moles of glycolaldehyde are reacted, 1 mole of glycolaldehyde remains (unreacted) in the product mixture, and 7 moles of monoethanolamine are present in this mixture, then (i) the conversion of glycolaldehyde is 90% (or 90 mole-%), (ii) the molar selectivity to monoethanolamine is 78%, (the formation of 7 moles of monoethanolamine resulting from the conversion 9 moles of glycolaldehyde), and (iii) the yield of monoethanolamine is 70%. Similar definitions of molar selectivity and yield apply to other reaction products.

Particular embodiments are directed to methods for producing monoethanolamine, comprising reacting glycolaldehyde (including forms of this compound as described above) with an aminating agent in the presence of both a hydrogenation catalyst and an acid co-catalyst under reductive amination conditions, to produce the monoethanolamine (e.g., in a product mixture from which the monoethanolamine may be recovered, such as in a purified form following one or more separation steps). A representative hydrogenation catalyst is a sponge metal catalyst, referring to a metal or metal alloy in granular or powder form. A preferred hydrogenation catalyst is a sponge nickel catalyst, with the material known as Raney nickel being exemplary. This catalyst is namely a fine-grained solid composed mostly of nickel that is present as a nickel-aluminum alloy. Hydrogenation catalysts may, more generally, include one or more hydrogenation-active metals, such as one or more transition metals selected from the group consisting of nickel (Ni), cobalt (Co), iron (Fe), and ruthenium (Ru). For example, representative hydrogenation catalysts may comprise at least 5% by weight (wt-%), typically at least 10 wt-%, and often at least 15 wt-%, of such metal(s). Such transition metal(s) may be disposed or deposited on a solid support, which is intended to encompass catalysts in which the active metal(s) is/are on the support surface and/or within a porous internal structure of the support. Therefore, in addition to such hydrogenation-active metal(s), representative hydrogenation catalysts may further comprise a solid support, with exemplary solid supports comprising one or more metal oxides, such as those selected from the group consisting of aluminum oxide, silicon oxide, titanium oxide, zirconium oxide, magnesium oxide, strontium oxide, tin oxide, etc. The solid support may comprise all, or substantially all of the one or more of such metal oxides, for example such that the one or more metal oxides are present in an amount, or combined amount, of at least 95% by weight of the solid support.

Importantly, aspects of the invention relate to advantages that may be attained when a hydrogenation catalyst (e.g., Raney nickel or others described above) is promoted with a co-catalyst having acidity, such as having acid sites in the case of a solid co-catalyst. The co-catalyst may, in particular, be a Lewis acid or have Lewis acid sites in the case of a solid co-catalyst. The density of Lewis acid sites may be measured according to known analytical methods, for example using pyridine-adsorbed Fourier transform infrared (FTIR) spectroscopy, on the basis of integral absorbance of the characteristic band at 1450 cm-1. This is described, for example, by Takagaki et al., THE ROYAL SOCIETY OF CHEMISTRY (RSC) ADVANCES (2014), Vol. 4:43785-91. Representative, solid acid co-catalysts, including those which are solid under the reductive amination conditions (and therefore in the presence of the reaction mixture) have a density of Lewis acid sites of generally from 50 to 2000 micromoles per gram (µmol/g), typically from 200 µmol/g to 1200 µmol/g, and often from 300 to 900 µmol/g. Unless otherwise noted, the term "acid" or "acidic," when used in reference to a solid co-catalyst, refers to its property of having acid sites, or ability to be titrated with a base (e.g., NaOH) in its "as prepared" form, for example outside of, or prior to, introduction into the reaction mixture used for reductive amination. This also applies with respect to references to particular ranges of acid site density. Without being bound by theory, it is believed that a certain level of acidity, which does not exceed a threshold level, is beneficial for enhancing selectivity to monoethanolamine in reactions described herein. With the knowledge gained from the present disclosure, those skilled in the art can optimize the level of acidity for a given set of reductive amination conditions.

Representative solid acid co-catalysts may comprise zeolitic or non-zeolitic molecular sieves, metal oxides, activated carbon, or resins. In the case of zeolitic molecular sieves, acidity is a function of the silica to alumina ($SiO_2$/$Al_2O_3$) molar framework ratio, with lower ratios corresponding to higher densities of acid sites. In embodiments in which the acid catalyst comprises a zeolitic molecular sieve (zeolite), its silica to alumina molar framework ratio may be less than 200 (e.g., from 5 to 200), or less than 100 (e.g., from 10 to 100). Particular solid acid catalysts may comprise one or more zeolitic molecular sieves (zeolites) having a structure type selected from the group consisting of FAU, FER, MEL, MTW, MWW, MOR, BEA, LTL, MFI, LTA, EMT. ERI, MAZ, MEI, and TON, and preferably selected from one or more of FAU, FER, MWW. MOR, BEA, LTL, and MFI. The structures of zeolites having these and other structure types are described, and further references are provided, in Meier, W. M, et al., *Atlas of Zeolite Structure Types*, 4$^{th}$ Ed., Elsevier: Boston (1996). Specific examples include zeolite Y (FAU structure), zeolite X (FAU structure), MCM-22 (MWW structure), ZSM-5 (MFI structure), and zeolite beta (BEA structure). Preferred are the structure types BEA and MFI.

Non-zeolitic molecular sieves include ELAPO molecular sieves are embraced by an empirical chemical composition, on an anhydrous basis, expressed by the formula:

$(EL_xAl_yP_z)O_2$, in which EL is an element selected from the group consisting of silicon, magnesium, zinc, iron, cobalt, nickel, manganese, chromium and mixtures thereof, x is the mole fraction of EL and is often at least 0.005, y is the mole fraction of aluminum and is at least 0.01, z is the mole fraction of phosphorous and is at least 0.01 and x+y+z=1. When EL is a mixture of metals, x represents the total amount of the element mixture present. The preparation of various ELAPO molecular sieves are well known in the art and may be found in U.S. Pat. No. 5,191,141 (ELAPO); U.S. Pat. No. 4,554,143 (FcAPO); U.S. Pat. No. 4,440,871 (SAPO); U.S. Pat. No. 4,853,197 (MAPO, MnAPO, ZnAPO, CoAPO); U.S. Pat. No. 4,793,984 (CAPO); U.S. Pat. Nos. 4,752,651 and 4,310,440. Representative ELAPO molecular sieves include ALPO and SAPO molecular sieves.

Other solid acid co-catalysts comprise carbon black or activated carbon, which may optionally be acidified to introduce a desired density of acid functional groups (e.g., by treatment with an appropriate functional group-bearing agent such as nitric acid, acetate, sulfonic acid, etc.). As such, these co-catalysts may generally be referred to acidic carbon or acidic activated carbon. The term "activated carbon" itself refers to a form of carbon that has been treated according to known techniques (e.g., steaming) to increase its surface area and pore volume. Similarly, such co-catalysts may comprise resins, such as ion-exchange resins that have acid functional groups. For example, resins within the group of Amberlyst™ Polymeric Catalysts have sulfonic functional groups. Other resins include those within the Dowex® group. The acidity of any of the types of solid acid co-catalysts described herein may be regulated or attenuated, if necessary, by treatment with a base such as ammonia or pyridine. For example, the zeolite ZSM-5 may be at least partially converted to its ammonium form by contacting with $NH_3$, thereby reducing the acidity, relative to the hydrogen form ZSM-5, to a desired level for a given reductive amination reaction. In general, therefore, ammonium form or ammonium-exchanged zeolites (e.g., $NH_4$-ZSM-5 or $NH_4$-BEA) may be used as acid co-catalysts, particularly those in which ammonia adsorption to provide these forms attenuates Lewis acid strength, such that the Lewis acid site density is adjusted or reduced to a value within the ranges given above. Alternatively, this regulation or attenuation of acidity may occur in situ in the reaction mixture, and particularly in the presence of the aminating agent such as ammonium hydroxide. Yet other solid acid co-catalysts useful for the present invention may comprise a metal oxide, such as any one or more of silica, alumina, titania, zirconia, magnesium oxide, calcium oxide, strontium oxide, tin oxide, etc. In the case of tin oxide, it may be present in hydrated and/or acidic forms, for example as metastannic acid or stannous acid.

Metal oxides are also described above in the context of being useful as solid supports for hydrogenation-active metals. Accordingly, it can be appreciated, more generally, that the "hydrogenation catalyst" and "acid co-catalyst" need not be in the form of separate catalysts, but can be present together in the form of particles of a solid, bi-functional catalyst. In such a bi-functional catalyst, (i) any "hydrogenation catalyst," or component thereof, as described above, may be present as a hydrogenation-active constituent of such bi-functional catalyst, and (ii) any "acid co-catalyst." or component thereof, as described above, may be present as an acidic constituent of such bi-functional catalyst. For example, a bi-functional catalyst may comprise any of the one or more hydrogenation active metals described above (e.g., nickel), deposited on any of the solid, acid co-catalysts described above (e.g., a zeolite or a metal oxide). The hydrogenation active metal(s) may be present in such bi-functional catalyst, as a hydrogenation-active constituent, in the amounts given above (e.g., at least 5 wt-%, based on the bi-functional catalyst weight), or possibly lower amounts (e.g., at least 2.5 wt-%, based on the bi-functional catalyst weight), as a result of integrating the two catalysts. The solid, acid co-catalyst, as an acidic constituent, may have a density of Lewis acid sites in the ranges given above (e.g., from 50 to 2000 µmol/g), or possibly lower ranges (e.g., from 25 to 1000), as a result of integrating the two catalysts.

Acid co-catalysts, and particularly Lewis acids, may be homogeneous in the reaction mixture, generally such that both the co-catalyst and reaction mixture are in the liquid phase (e.g., in the case of the co-catalyst being solubilized). According to a particular embodiment, the co-catalyst is solubilized in an aqueous liquid reaction mixture, comprising aqueous ammonia (ammonium hydroxide) as the aminating agent. Representative soluble acid co-catalysts are metallic trifluoromethylsulfonates, otherwise known as metal triflates. Specific examples include the triflates of the 15 lanthanide elements, as well as triflates of scandium and yttrium. According to a particular embodiment, a triflate co-catalyst may be selected from the group consisting of bismuth (Bi) triflate, gallium (Ga) triflate, copper (Cu) triflate, europium (Eu) triflate, silver (Ag) triflate, indium (In) triflate, cerium (Ce) triflate, gadolinium (Gd) triflate, erbium (Er) triflate, aluminum (Al) triflate, and mixtures of any two or more of these triflates. Other examples of co-catalysts that act as homogeneous Lewis acids include ammonium compounds other than ammonium hydroxide when used as the aminating agent. Ammonium acetate and ammonium chloride are exemplary.

Whether or not the acid co-catalyst is solid (heterogeneous) in the reaction mixture, liquid (homogeneous) in the reaction mixture, solid and separate from the hydrogenation catalyst, or solid and integrated with the hydrogenation catalyst, aspects of the present invention relate to improvements in methods for the reductive amination of glycolaldehyde, resulting from the use of the acid co-catalyst. Particular improvements are increased selectivity to the desired compound, monoethanolamine, and/or decreased selectivity to undesired byproducts, such as the dimerized byproduct, diethanolamine, and/or the hydrogenated byproduct, ethylene glycol. The amount of acid co-catalyst for obtaining a given effect (e.g., selectivity improvement) is dependent on the particular acid co-catalyst used and given set of reductive amination conditions, and with the knowledge gained from the present disclosure, those skilled in the art can determine a suitable amount in each case. Generally, any acid co-catalyst described above, or combination of acid co-catalysts, may be present in the reaction mixture, including the hydrogenation catalyst and solvent such as water, in an amount, or combined amount, generally from 0.1 wt-% to 99 wt-%. More typically, co-catalyst(s) may be present in an amount or combined amount from 0.1 wt-% to 20 wt-%, such as from 0.3 wt-% to 15 wt-% or from 0.5 wt-% to 10 wt-%. In the case of a continuous process, the acid co-catalyst may be present in an amount needed to achieve a weight hourly space velocity (WHSV) with respect to this catalyst, as described below. The acid co-catalyst, as well as the hydrogenation catalyst, and optionally a bi-functional catalyst having integrated constituents as described herein, can be prepared by any method known in the art including, for example, impregnation/incipient wetness, co-precipitation, or hydrothermal.

Representative processes are therefore characterized by comparatively high selectivities to monoethanolamine, relative to conventional processes in which the acid co-catalysts described above are not present or if present are not utilized in the manner described above and exemplified below. According to particular embodiments, glycolaldehyde may be converted with a molar selectivity to monoethanolamine of 45% or more to 98% or less, in other embodiments of 55% or more to 94% or less, and in other embodiments of 70% or more to 90% or less. In particular embodiments, the molar selectivity to MEA is at least 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97 or 98 percent. Such selectivities may be associated with comparably low selectivities to the dimerized byproduct, diethanolamine. According to particular embodiments, glycolaldehyde may be converted with a molar selectivity to diethanolamine of less than 20%, less than 10%, or less than 5%, for example, less than 20, 19, 18, 17, 16, 15, 14, 13, 12, 11, 10, 9, 8, 7, 6 or 5 percent. Alternatively, the selectivity improvement may be characterized with respect to a reference molar selectivity, obtained from a reference process in which all reductive amination conditions (e.g., pressure, temperature, residence time, feeds (including aminating agent), catalyst(s), etc.) are identical, except for the absence of the acid co-catalyst. According to particular embodiments, glycolaldehyde may be converted with a molar selectivity to monoethanolamine, which exceeds a reference molar selectivity by at least 3%. That is, in the case of a reference molar selectivity of 50%, the use of the acid co-catalyst results in a molar selectivity that is increased to at least 53%. In other embodiments, glycolaldehyde may be converted with a molar selectivity to monoethanolamine, which exceeds a reference molar selectivity by at least 5%, or even at least 10%, for example, at least 3, 4, 5, 6, 7, 8, 9 or 10 percent. Those skilled in the art will appreciate that even modest increases in selectivity can potentially result in substantial economic benefits on the commercial scale.

The molar selectivities described above may be obtained at high levels of conversion of glycolaldehyde. According to particular embodiments, the glycolaldehyde conversion may be at least 85%, at least 90%, at least 95%, or even at least 99%, thus at least 85, 86, 87, 88, 89, 90, 91, 92, 93, 94, 95, 96, 97, 98 or 99 percent. Accordingly, representative yields of monoethanolamine may be the same or substantially the same as the molar selectivity ranges given above, such as 45% or more to 98% or less, in other embodiments 55% or more to 94% or less, or in other embodiments 70% or more to 90% or less of the theoretical yield obtainable, given that yield is determined as the product of conversion and selectivity.

Typical reductive amination conditions include an elevated hydrogen partial pressure, such as at least 3 megapascals (MPa) (435 psi), which, in combination with the hydrogenation catalyst and acid co-catalyst, provide a reductive amination environment for carrying out the conversion of glycolaldehyde, selectively to the product monoethanolamine. This hydrogen pressure may be contained in a reactor that is used for the contacting of the feed (e.g., an aqueous feed comprising glycolaldehyde) and an aminating agent (e.g., aqueous ammonia), with the catalysts (or bi-functional catalyst as described above) to obtain this product. The reaction mixture, to which the feed and aminating agent are added and from which a product mixture is withdrawn (e.g., following separation from the catalyst(s)) is preferably aqueous and comprises dissolved hydrogen under the reductive amination conditions. As described above, the acid co-catalyst may be homogeneous or heterogeneous in the reaction mixture. In addition, or alternatively, to aqueous ammonia, the aminating agent may otherwise comprise gaseous ammonia that may be added batchwise or continuously to the reactor, for example it may be added, in the case of continuous operation, with hydrogen or a recycle gas stream comprising hydrogen. The addition of gaseous ammonia will generally cause the in situ formation of aqueous ammonia in the presence of an aqueous reaction mixture. Other possible aminating agents include primary and secondary amines of the formula $NHR^1R^2$, wherein at least one of $R^1$ and $R^2$ is a $C_1$-$C_3$ alkyl group. The glycolaldehyde and aminating agent may be charged to the reactor batchwise, or otherwise continuously added to the reactor, with a molar excess of the aminating agent, for example, with an aminating agent:glycolaldehyde molar ratio of from 2:1 to 20:1 or from 5:1 to 15:1.

Reductive amination conditions, under which the reaction mixture is maintained during the production of monoethanolamine, include an elevated pressure and hydrogen partial pressure. Representative absolute reactor pressures are in the range generally from 2.07 MPa (300 psi) to 24.1 MPa (3500 psi), typically from 3.45 MPa (500 psi) to 20.7 MPa (3000 psi), and often from 5.17 MPa (750 psi) to 10.3 MPa (1500 psi). The reactor pressure may be generated predominantly or substantially from hydrogen, such that these ranges of total pressure may also correspond to ranges of hydrogen partial pressure. However, the presence of gaseous ammonia or other aminating agent, as well as other gaseous species vaporized from the reaction mixture, may result in the hydrogen partial pressure being reduced relative to these total pressures, such that, for example, the hydrogen partial pressure may range generally from 1.38 MPa (200 psi) to 22.4 MPa (3250 psi), typically from 3.00 MPa (435 psi) to 20.0 MPa (2901 psi), and often from 4.82 MPa (700 psi) to 9.31 MPa (1350 psi).

Other reductive amination conditions, present in the reactor, include a temperature generally from 20° C. (68° F.) to 200° C. (392° F.), and typically from 50° C. (122° F.) to 150° C. (302° F.). The reaction time, i.e., time at which the reaction mixture is maintained under conditions of pressure and temperature at any target values or target sub-ranges within any of the ranges of pressure and temperature given above (e.g., a target, total pressure value of 8.27 MPa (1200 psi) and a target temperature of 85° C. (185° F.), is from 0.5 hours to 24 hours, and preferably from 1 hour to 5 hours, in the case of a batchwise reaction. For a continuous process, these reaction times correspond to reactor residence times. An additional parameter that is relevant for a continuous process is weight hourly space velocity (WHSV), which is understood in the art as the weight flow of the feed (e.g. aqueous feed comprising glycolaldehyde and $NH_4OH$) to a reactor, divided by the catalyst weight (e.g., combined weight of the hydrogenation catalyst and acid co-catalyst, or weight of a bi-functional catalyst). This parameter therefore represents the equivalent catalyst bed weight of the feed processed every hour, and it is related to the inverse of the reactor residence time. According to representative embodiments, the reductive amination conditions include a WHSV generally from 0.01 $hr^{-1}$ to 20 $hr^{-1}$, and typically from 0.05 $hr^{-1}$ to 5 $hr^{-1}$. However, with respect to the acid co-catalyst alone, these ranges may be higher, for example generally from 0.02 $hr^{-1}$ to 40 $hr^{-1}$, and typically from 0.1 $hr^{-1}$ to 10 $hr^{-1}$.

As described above, a continuous process, such as a continuous fixed bed process, may be more compatible with a heterogeneous acid co-catalyst (e.g., comprising a molecular sieve, activated carbon, metal oxide, or resin, having a requisite density of Lewis acid sites). Such a continuous process may be performed by continuous feeding of glycolaldehyde, aminating agent, and hydrogen to the reaction mixture comprising the catalyst(s) and contained within the reactor, and continuous withdrawal, from the reactor, of a product mixture comprising monoethanolamine and substantially free of the catalyst(s). This product mixture may then be further processed by separating portions of the product mixture to purify and recover the monoethanolamine and optionally recycle unconverted reactants, such as the aminating agent and/or hydrogen. According to one embodiment, the product mixture may be subjected to flash separation to separate a primarily hydrogen-containing vapor phase, at least portion of which (e.g., following the removal of a purge stream to prevent excessive accumulation of unwanted impurities) may provide the recycle gas stream, described above. The liquid phase recovered from the flash separation and also comprising the desired monoethanolamine, may be subjected to any of a number of possible separation steps, including one or more of phase separation, extraction (e.g., using an organic solvent having preferential affinity for monoethanolamine), and distillation, sequentially in any order. Extraction and distillation may alternatively be combined in a single, extractive distillation step. As with the recycle gas stream, any separated liquid products (e.g., aminating agent and/or unconverted glycolaldehyde) may likewise be recycled to the reactor. Whether performed batchwise or continuously, particular embodiments relate to methods for producing monoethanolamine, comprising performing a reductive amination of glycolaldehyde, added to an aqueous reaction mixture with aqueous ammonia as a reactant. This may be performed by contacting this reaction mixture and hydrogen with both a hydrogenation catalyst and an acid co-catalyst (e.g., contacting both catalysts simultaneously) under reductive amination conditions as described above. Advantageously, the catalysts in combination, or otherwise constituents of a bi-functional catalyst in combination, catalyze the reductive amination to produce monoethanolamine according to any of the conversion, selectivity, and yield performance criteria described above, such as a yield of at least 70% of a theoretical yield.

According to further embodiments, the production of monoethanolamine may be integrated with upstream and/or downstream processing steps in the overall production of chemicals, for example sourced from biomass. In the case of integration with upstream processing, the glycolaldehyde may be obtained from the pyrolysis of an aldose or a ketose (e.g., glucose, fructose, or sucrose). In the case of downstream processing, representative methods may further comprise sulfating at least a portion of the monoethanolamine (e.g., following its recovery from a product mixture described above) to produce 2-aminoethyl sulfuric acid. A convenient sulfating agent for this conversion is sulfuric acid, and the sulfate ester of this first conversion step is prepared favorably under conditions in which the co-generated water is removed as quickly and completely from the reaction mixture as possible, driving the equilibrium toward 2-aminoethylsulfuric acid production. In this case, representative methods may also comprise sulfonating at least a portion of the 2-aminoethyl sulfuric acid (e.g., following its recovery from a product mixture obtained from the sulfating) to produce taurine. A suitable reagent for the sulfonation step, performed in aqueous solution with continual heating, is sodium sulfite. A representative two-step process, with details of the synthesis conditions at each step, is described, for example, by Bondareva et al., PHARMACEUTICAL CHEMISTRY JOURNAL, 42 (3): 142-144. In this manner, a viable synthesis method for taurine from a renewable carbon source is established.

The following examples are set forth as representative of the present invention. These examples are not to be construed as limiting the scope of the invention as other equivalent embodiments will be apparent in view of the present disclosure and appended claims.

EXAMPLE 1

Example 1—Al-Triflate Co-Catalyst, Synthesis of Monoethanolamine from Glycolaldehyde The following were charged to a 100 ml Parr reactor, made of Hastelloy: 1 gram of glycolaldehyde dimer, 1.5 grams of wet Raney nickel (W.R. Grace & Co.), and 0.18 grams of aluminum tris(trifluoromethanesulfonate) (Al-Triflate) in 20 ml of $NH_4OH$ (28%). The reactor was purged twice with $N_2$, and then charged with 6.2 MPa (900 psi) $H_2$. The reaction mixture was stirred at 1100 rpm for 2 hours at 85° C. (185° F.). After this time period, the reactor was cooled to room temperature, and the reaction mixture filtered to separate the nickel catalyst from a colorless product mixture. The calculated yields based on gas chromatograph (GC) analysis of this mixture were 93% monoethanolamine yield, 2% ethylene glycol yield, and 0.5% diethanolamine yield.

Figure 1:
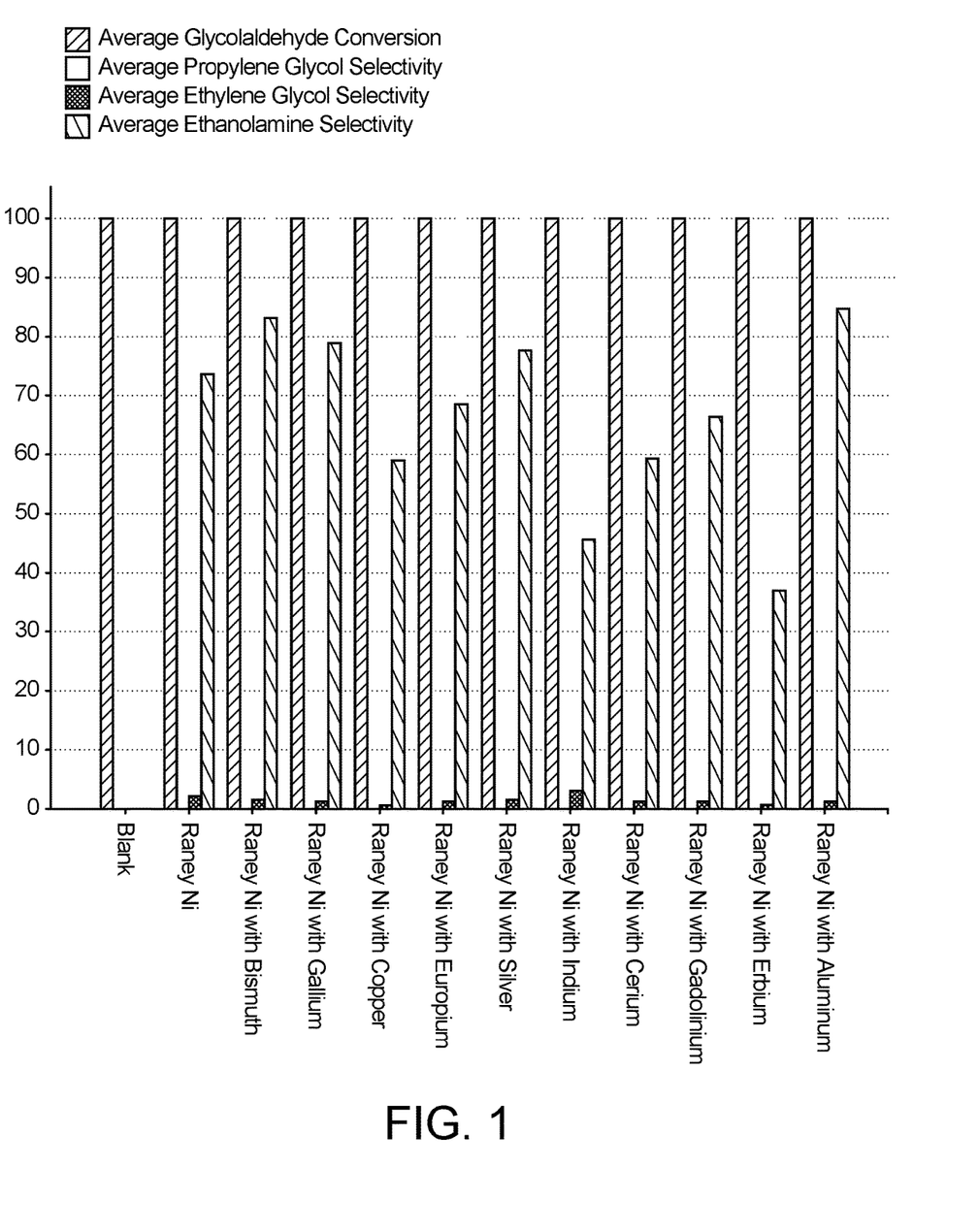
FIG. 1 is a bar graph of conversion and product selectivity values, obtained in experiments performing the reductive amination of glycolaldehyde (i) in the absence of a catalyst, (ii) in the presence of Raney nickel alone, and (iii) in the presence of both Raney nickel and a metal triflate as a co-catalyst.

Example 2—Metal-Triflate Co-Catalysts, Synthesis of Monoethanolamine from Glycolaldehyde A number of experiments were conducted to investigate the performance of various metal trifluoromethanesulfonates (triflates) as solubilized (homogeneous) co-catalysts. In each case, a feed comprising 5% glycolaldehyde dimer by weight in 28% aqueous ammonia solution was reacted, together with a fixed amount of Raney nickel and the metal triflate, in a high throughput screening batch reactor. Reference experiments were also performed without either of the Raney nickel catalyst or metal triflate co-catalyst, as well as with Raney nickel catalyst alone (in the absence of a metal triflate co-catalyst). The catalytic, reductive amination reactions were carried out in sealed hydrogenolysis reactors at 85° C. (185° F.) and under 8.27 MPa (1200 psi) hydrogen pressure for a 2 hour hold period. The reaction product, following the separation from solid catalyst, was analyzed by GC. The results demonstrated that selectivity for monoethanolamine could be enhanced using metal triflates as co-catalysts, compared to the use of Raney nickel alone. The results, including glycolaldehyde conversion levels, selectivities to the byproducts propylene glycol and ethylene glycol, and selectivities to monoethanolamine, are shown in FIG. 1.

Figure 2:
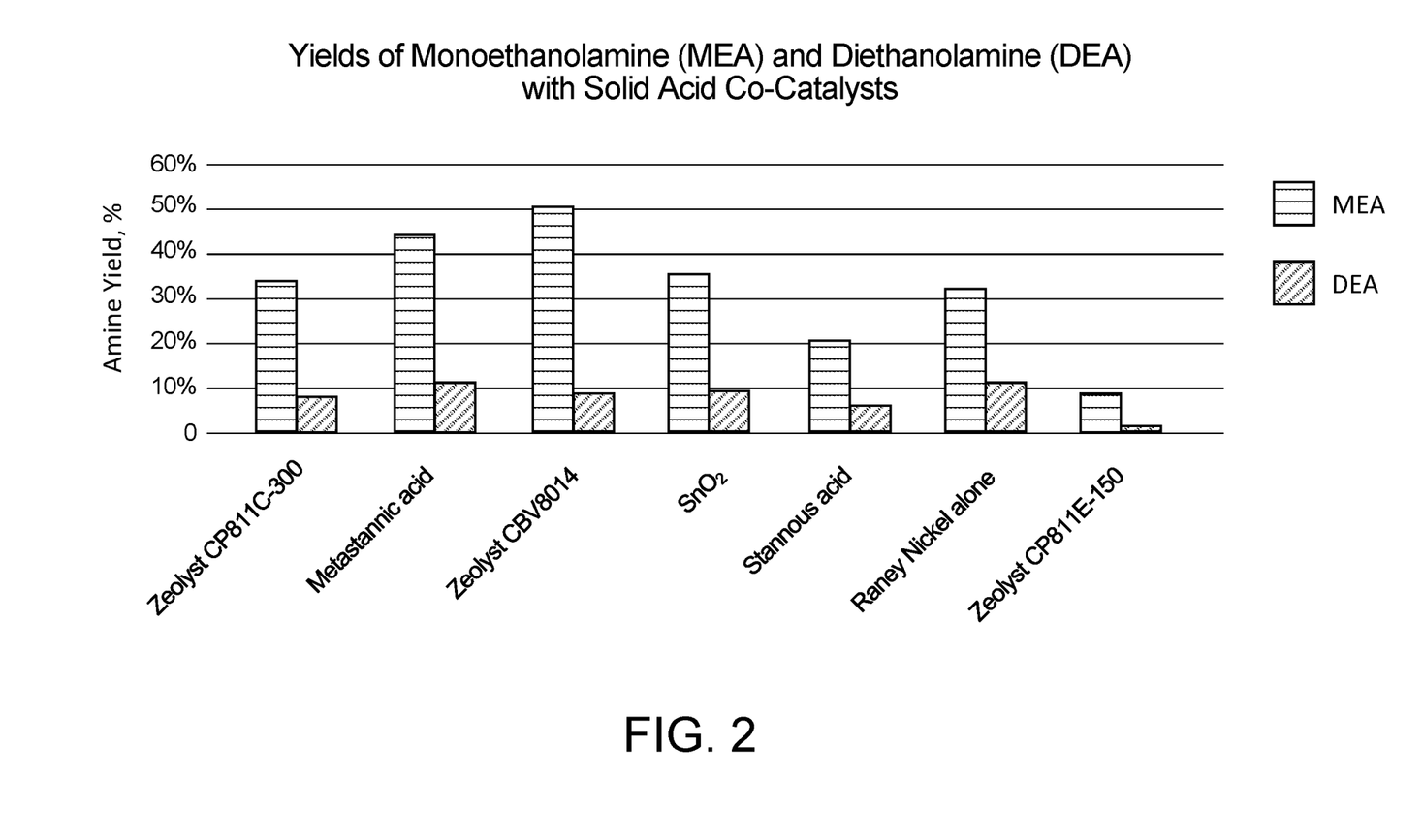
FIG. 2 is a bar graph of monoethanolamine and diethanolamine yield values, obtained in experiments performing the reductive amination of glycolaldehyde (i) in the presence of Rancy nickel alone, and (ii) in the presence of both Raney nickel and various solid acid co-catalysts.

Example 3—Solid Acid Co-Catalysts, Synthesis of Monoethanolamine from Glycolaldehyde A number of experiments were conducted to investigate the performance of various solid (heterogeneous) acid co-catalysts. In each case, a feed comprising 5% glycolaldehyde dimer by weight in 28% aqueous ammonia solution was reacted, together with a fixed amount of Raney nickel and the solid acid co-catalyst, in a high throughput screening batch reactor. A reference experiment was also performed with Raney nickel catalyst alone (in the absence of a solid acid co-catalyst). The catalytic, reductive amination reactions were carried out in sealed hydrogenolysis reactors at 85° C. (185° F.) and under 8.27 MPa (1200 psi) hydrogen pressure for a 2 hour hold period. The reaction product, following the separation from solid catalyst(s), was analyzed by GC. The results demonstrated that selectivity for, and consequently the yield of, monoethanolamine could be enhanced using solid acid co-catalysts, including zeolites and solid acids, such as acidified activated carbon and hydrated or acidic forms of tin oxide, compared to the use of Raney nickel alone. The ethanolamine and diethanolamine yield results for the various solid acid co-catalysts are shown in FIG. 2.

Figure 3:
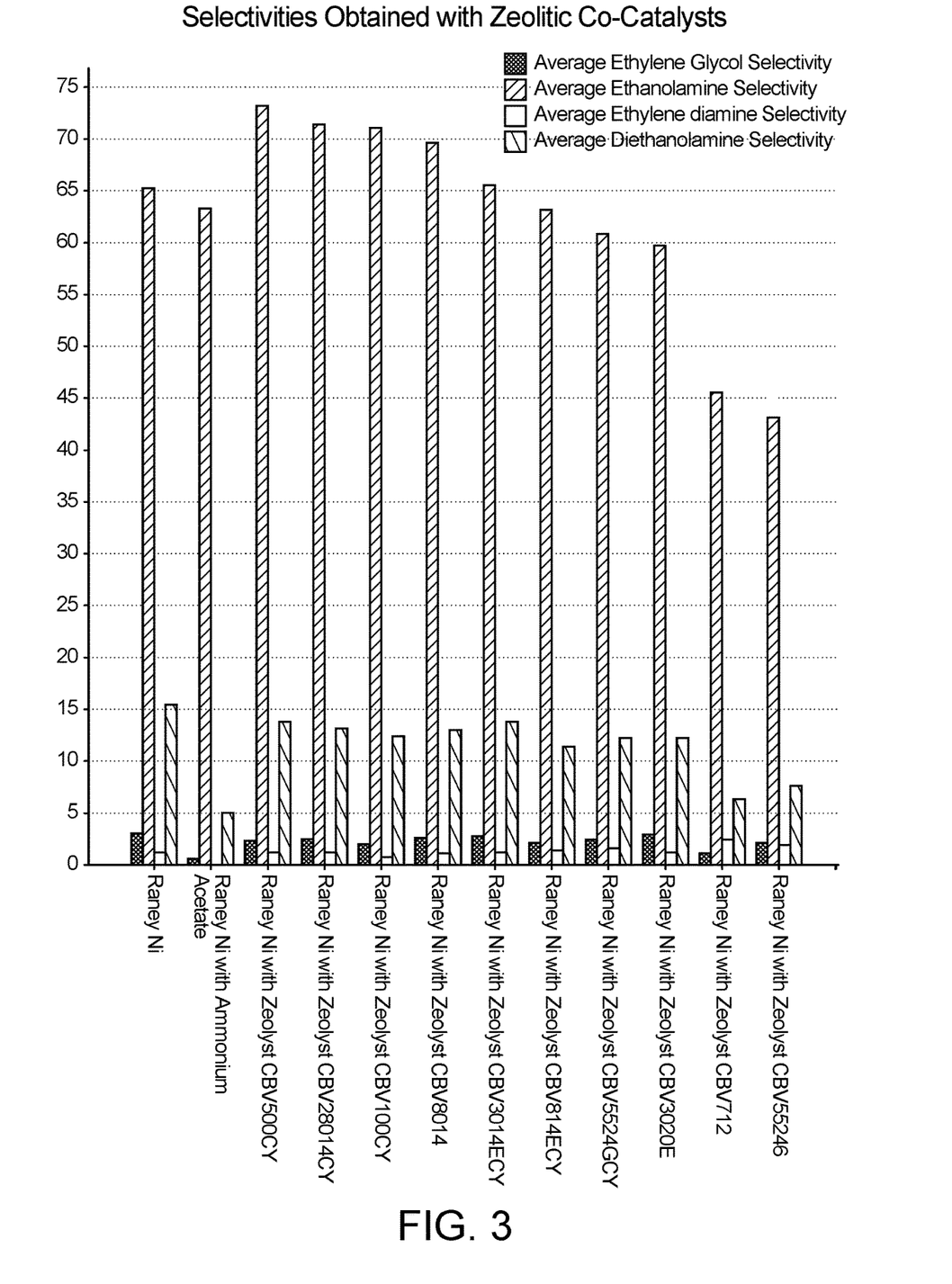
FIG. 3 is a bar graph of product selectivity values, obtained in experiments performing the reductive amination of glycolaldehyde (i) in the presence of Raney nickel alone, and (ii) in the presence of both Raney nickel and various zeolites as solid acid co-catalysts.

Example 4—Zeolitic Co-catalysts, Synthesis of Monoethanolamine from Glycolaldehyde A number of experiments were conducted to investigate the performance of various zeolites, as solid (heterogeneous) acid co-catalysts. In each case, a feed comprising 5% glycolaldehyde dimer by weight in 28% aqueous ammonia solution was reacted, together with a fixed amount of Raney nickel and the zeolite, in a high throughput screening batch reactor. A reference experiment was also performed with Raney nickel catalyst alone (in the absence of a zeolite). Another experiment as performed with Raney nickel and ammonium acetate as a homogeneous co-catalyst. The catalytic, reductive amination reactions were carried out in sealed hydrogenolysis reactors at 85° C. (185° F.) and under 8.27 MPa (1200 psi) hydrogen pressure for a 2 hour hold period. The reaction product, following the separation from solid catalyst(s), was analyzed by GC. The results demonstrated that selectivity for monoethanolamine could be enhanced using zeolites, as solid (heterogeneous) acid co-catalysts, compared to the use of Raney nickel alone. The results including the selectivities to monoethanolamine, as well as selectivities to the byproducts ethylene glycol, ethylene diamine, and diethanolamine, are shown in FIG. 3.

Overall, aspects of the invention relate to increases in reaction selectivity to monoethanolamine, by reductive amination of glycolaldehyde, which can be achieved using various acid co-catalysts. Efficiencies and the associated economics of synthesis pathways from renewable feeds to high value chemicals are thereby improved. Those having skill in the art, with the knowledge gained from the present disclosure, will recognize that various changes can be made to the disclosed catalysts and processes in attaining these and other advantages, without departing from the scope of the present disclosure. As such, it should be understood that the features of the disclosure are susceptible to modifications and/or substitutions. The specific embodiments illustrated and described herein are for illustrative purposes only, and not limiting of the invention as set forth in the appended claims.

The invention claimed is:
1. A method for producing monoethanolamine, the method comprising:
    reacting glycolaldehyde with an aminating agent in the presence of both a hydrogenation catalyst and an acid co-catalyst under reductive amination conditions, to produce said monoethanolamine; wherein
    said hydrogenation catalyst and acid co-catalyst are solid,
    said hydrogenation catalyst is Raney nickel, and
    said acid co-catalyst comprises a zeolitic molecular sieve having a silica to alumina molar framework ratio of less than 200.

2. The method of claim 1, wherein the reductive amination conditions include a temperature from 20° C. to 200° C., a hydrogen partial pressure from 3 MPa to 20 MPa and a residence time from 0.5 hours to 10 hours.

3. The method of either claim 1 or claim 2, wherein the reacting occurs in an aqueous reaction mixture, to which said glycolaldehyde and said aminating agent are added.

4. The method of claim 3, wherein the acid co-catalyst is a solid in the aqueous reaction mixture.

5. The method of claim 4, wherein the acid co-catalyst has a density of Lewis acid sites from 200 to 1200 μmol/g.

6. The method of claim 1, wherein said acid co-catalyst is a zeolitic molecular sieve having a structure type selected from the group consisting of FAU, fer, mel, mtw, MWW, mor, BEA, ltl, MFI, lta, emt, eri, maz, mei, and ton.

7. The method of claim 6, wherein the structure type is BEA or MFI.

8. The method of claim 1, wherein the glycolaldehyde is obtained from pyrolysis of an aldose or a ketose.

9. The method of claim 1 or claim 8, further comprising: sulfating at least a portion of said monoethanolamine to produce 2-aminoethyl sulfuric acid; and sulfonating at least a portion of said 2-aminoethyl sulfuric acid to produce taurine.

* * * * *